United States Patent [19]

Burk, Jr. et al.

[11] 3,979,401

[45] Sept. 7, 1976

[54] POLYFUNCTIONAL ALIPHATIC AND CYCLOALIPHATIC CYCLIC NITRILE SULFITES AND CARBONATES

[75] Inventors: Emmett H. Burk, Jr., Glenwood, Ill.; Donald D. Carlos, Middletown, Ky.

[73] Assignee: Atlantic Richfield Company, Los Angeles, Calif.

[22] Filed: Feb. 27, 1974

[21] Appl. No.: 442,706

Related U.S. Application Data

[63] Continuation of Ser. No. 134,043, April 14, 1971, abandoned, which is a continuation-in-part of Ser. No. 713,997, March 18, 1968, abandoned, which is a continuation-in-part of Ser. No. 502,327, Oct. 22, 1965, abandoned, and Ser. No. 502,464, Oct. 22, 1965, abandoned.

[52] U.S. Cl................................. 260/301; 260/240 R; 260/240 E; 260/240.1; 260/307 A; 260/453 P
[51] Int. Cl.²......................................... C07D 291/04
[58] Field of Search............ 260/301, 307 A, 240 E, 260/240 R, 240.1

[56] References Cited

UNITED STATES PATENTS

| 2,394,597 | 2/1946 | Dickey et al.............. | 260/301 |
| 3,560,492 | 2/1971 | Burk et al................. | 260/307 A |

*Primary Examiner*—Richard J. Gallagher
*Attorney, Agent, or Firm*—Coleman R. Reap

[57] ABSTRACT

The disclosure is of compounds of the formula:

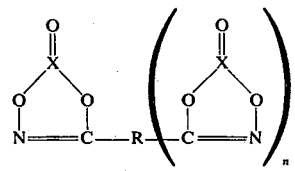

wherein R is aliphatic hydrocarbon, X is sulfur (S) or carbon (C) and $n$ is an integer of 1 to 3. The compounds are useful as easily-storable, polyisocyanate generators, especially the essentially-chlorine free compounds.

6 Claims, No Drawings

POLYFUNCTIONAL ALIPHATIC AND CYCLOALIPHATIC CYCLIC NITRILE SULFITES AND CARBONATES

This application is a continuation of application Ser. No. 134,043 filed Apr. 14, 1971, now abandoned, which in turn is a Continuation-in-Part of application Ser. No. 713,997 filed Mar. 18, 1968, now abandoned, which in turn is a Continuation-in-Part of application, Ser. Nos. 502,327 and 502,464, both filed Oct. 22, 1965, both now abandoned.

This present invention is directed to cyclic nitrile sulfite or nitrile carbonate compounds of the structural formula:

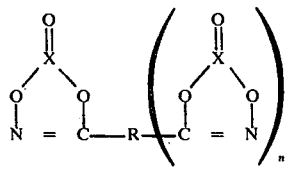

wherein R is aliphatic or cycloaliphatic hydrocarbon of 1 to 30 carbon atoms, X is S (sulfur) or C (carbon), and $n$ is an integer of 1 to 3, preferably 1. The hydrocarbon, R, can be saturated or unsaturated, straight or branched chain and can be substituted with non-interfering groups, there often being no more than about 2 of such groups; it is free, however, of any isocyanate-reactive hydrogen atoms. Preferably the hydrocarbon, R, is alkyl, cycloalkyl or monoolefinic. the nitrile sulfite or nitrile carbonate groups may be attached to the same or different carbon atoms of the hydrocarbon, R, but preferably the hydrocarbon, R, contains a nitrile sufilte or carbonate group on each end of the longest carbon chain, and preferably no more than two, or even only one, of such groups on a given carbon atom.

The aliphatic and cycloaliphatic poly(nitrile sulfites) and poly(nitrile carbonates) of the present invention are valuable intermediates or precursors for the preparation of highly desired chemicals. For example, these cyclic compounds can be thermally decomposed to polyisocyanates. Polyisocyanates, such as diisocyanates, have found extensive use in the preparation of high molecular weight polymers by reaction of the polyisocyanates with polymerizable organic compounds such as compounds with terminally active hydroxy and amine groups. Polyurethanes, for instance, are commonly prepared by the reaction of diisocyanates and polybasic alcohols such as the glycols. The poly(nitrile sulfites) and poly(nitrile carbonates) of the invention can also be acid hydrolyzed to hydroxamic acids.

Decomposition of the aliphatic and cycloaliphatic poly(nitrile sulfites) or poly(nitrile carbonates) to the corresponding polyisocyanates can be effected by heating the cyclic compounds. The yield of polyisocyanates is particularly enhanced when the aliphatic and cycloaliphatic poly(nitrile sulfites) and poly(nitrile carbonates) decomposed are essentially free of chlorine. Thus, these poly(nitrile sulfite) or poly(nitrile carbonate) products contain less than 0.1 weight percent chlorine, preferably less than 0.05 or even less than 0.03, weight percent, as chlorine-containing impurities. Such impurities may result from side reactions involving the chlorine-containing reactants, for instance, thionyl chloride or phosgene, used in preparing the compounds of this invention. The objectionable, chlorine-containing impurities seem to be characterized by molecular structures in which chlorine is attached to an atom other than a carbon atom. The compounds of the invention are similarly free of other halogen-containing impurities. The hydrocarbon di(nitrile sulfites) and di(nitrile carbonates) which are essentially free of chlorine or other halogen, i.e. having less than 0.1, preferably less than 0.05 or even less than 0.03, weight percent, are of particular interest as precursors for hydrocarbon diisocyanates.

The decomposition reaction which produces the polyisocyanates can be conducted either in the presence or absence of catalyst, at a temperature below the degradation point of the desired polyisocyanate product. Degradation may be evidenced by conversion to organic by-products, and the extent of degradation at elevated temperatures can be a function of the time the product is held at such temperatures. Thus, degradation can be a time-temperature relationship, the latter being controlled to prevent undue degradation of the desired product. Since the decomposition reaction is exothermic, there may be a tendency for the reaction temperature to run away. Means for carrying away or absorbing heat may be used, therefore, to control the temperature below the degradation point of the desired polyisocyanate product. The temperature employed will vary, of course, depending upon the decomposition temperature of the feed and degradation temperature of the particular polyisocyanates being prepared. Generally, for instance, the poly(nitrile sulfites) are more readily decomposed to their corresponding polyisocyanates than are the nitrile carbonates ot the invention; conversion of the latter to isocyanates will usually, therefore, require the use of higher temperatures than are required for conversion of the nitrile sulfites. Thus, for example, decomposition temperatures as high as about 325°C. or higher may be required in the case of the nitrile carbonates, whereas with the nitrile sulfites, decomposition temperatures will more usually be in the range of about 50° to 200°C., often about 75° to 150°C.

Advantageously, the decomposition is conducted in the presence of an inert solvent such as benzene, xylenes, toluene, chlorobenzene, polyphenyl ether, and the like, the solvent serving as a heat sink and preventing the formation of hot spots in the decomposition zone. Where relatively high decomposition temperatures are required, so that problems of product degradation are posed, isocyanate yields can be enhanced by removing the isocyanate product from the decomposition zone as soon as it is formed. This may be accomplished, for example, by conducting the decomposition at reduced pressures and in the presence of a high boiling, inert solvent and effecting flash vaporization and overhead collection of the isocyanate product. Such flash vaporization can be accomplished, for instance, by gradually adding the cyclic nitrile carbonate or sulfite, preferably as a solution in an inert solvent, to the surface of a pool, or heel, of the high boiling solvent which is maintained at decomposition temperatures. Continuous removal and collection of the flash vapors of isocyanate product can be by known methods and with known equipment.

The ability of the aliphatic and cycloaliphatic cyclic compounds of the invention to generate polyisocyanates upon heating, provides an additional advantage to the consumer in that the cyclic compounds of the invention, in contrast to isocyanates, are stable in the absence of water and therefore can be easily handled and stored. Also, since there is no active hydrogen (e.g. in the form of HCl) present in the poly(nitrile sulfites) and poly(nitrile carbonates) of the invention, or in the decomposition products formed, to react with the isocyanate when the latter is made, use of the cyclic compounds for the production of polyisocyanates provides a method that does not suffer from the reduced yields and separation and purification problems presented by the by-products obtained from starting materials of commercial methods wherein active hydrogen is present. Use of these cyclic compounds in the preparation of isocyanates, furthermore, provides a process having advantages over commercial methods employing azides in that the former do not have the explosion tendencies of the latter and are more economical. Other and more detailed methods of using the cyclic compounds of the present invention are disclosed in U.S. patent application Ser. No. 592,288 of Burk, Jr., et al., filed Nov. 7, 1966, now U.S. Pat. No. 3,531,425, herein incorporated by reference.

The aliphatic and cycloaliphatic poly(nitrile sulfites) of the invention can be prepared by reacting an aliphatic or cycloaliphatic polyhydroxamic acid and thionyl chloride, while the aliphatic or cycloaliphatic poly(nitrile carbonates) can be prepared by reacting an aliphatic or cycloaliphatic polyhydroxamic acid and phosgene. Polyhydroxamic acids which react with thionyl chloride or phosgene to produce the novel compounds of the invention can be represented by the structure:

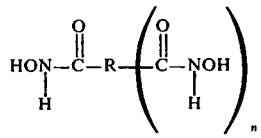

wherein R and n are as defined above in the structure of the aliphataic and cycloaliphatic compounds of the invention.

Illustrative of polyhydroxamic acids suitable for use as the reactant in the preparation of the aliphatic and cycloaliphatic poly(nitrile sulfites) and poly(nitrile carbonates) of the invention are the following: malonodihydroxamic acid; succinodihydroxamic acid; glutarodihydroxamic acid; adipodihydroxamic acid; pimelodihydroxamic acid; suberodihydroxamic acid; azelaodihydroxamic acid; sebacodihydroxamic acid; fumarodihydroxamic acid; itaconodihydroxamic acid; allylmalonodihydroxamic acid; allylsuccinodihydroxamic acid; xeronodihydroxamic acid; cetylmalonodihydroxamic acid; thapsodihydroxamic acid; japanodihydroxamic acid; 1,6,9-decanetrihydroxamic acid; 1,3,6-heptanetrihydroxamic acid; cyclohexyldihydroxamic acid; 4-bromo-1,6-hexanedihydroxamic acid; 2-chloro-1.9-nonanedihydroxamic acid; di- and trihydroxamic acids prepared from dimers or trimers of long chain, ethylenically-unsaturated, monocarboxylic acids, i.e., fatty acid dimers and trimers such as linoleic acid dimer and trimer, including hydrogenated dimers and trimers thereof; etc. Preparation of the polyhydroxamic acid starting materials can be by methods known in the art, such as, for instance, by the reaction of hydroxylamine with the corresponding polycarboxylic acid halides or with the lower alkyl esters of the corresponding polycarboxylic acids.

Illustrative examples of poly(nitrile sulfites) of the invention include those corresponding to the foregoing hydroxamic acids such as malonodi(nitrile sulfite); succinodi(nitrile sulfite); glutarodi(nitrile sulfite); adipodi(nitrile sulfite); pimelodi(nitrile sulfite); suberodi(nitrile sulfite); azelaodi(nitrile sulfite); sebacodi(nitrile sulfite); fumarodi(nitrile sulfite); itaconodi(nitrile sulfite); allylmalonodi(nitrile sulfite); allylsuccinodi(nitrile sulfite); xeronodi(nitrile sulfite); cetylmalonodi(nitrile sulfite); thapsodi(nitrile sulfite); japanodi(nitrile sulfite); 1,6,9-decanetri(nitrile sulfite); 1,3,6-heptanetri(nitrile sulfite); 4-bromo-1,6-hexanedi(nitrile sulfite); 2-chloro-1,9-nonanedi(nitrile sulfite); cyclohexyldi(nitrile sulfite); dilinoleodi(nitrile sulfite); trilinoleotri(nitrile sulfite); etc. (Alternatively, the foregoing poly(nitrile sulfites) may be named as nitrile polysulfites; for instance, fumarodi(nitrile sulfite) might also be designated as "fumaronitrile disulfite," and so forth).

Similarly, illustrative examples of poly(nitrile carbonates) of the invention include those corresponding to the foregoing hydroxamic acids such as malonodi(nitrile carbonate); succinodi(nitrile carbonate); glutarodi(nitrile carbonate); adipodi(nitrile carbonate); pimelodi(nitrile carbonate); suberodi(nitrile carbonate); azelaodi(nitrile carbonate); sebacodi(nitrile carbonate); fumarodi(nitrile carbonate); itaconodi(nitrile carbonate); allylmalonodi(nitrile carbonate); allylsuccinodi(nitrile carbonate); xeronodi(nitrile carbonate); cetylmalonodi(nitrile carbonate); thapsodi(nitrile carbonate); japanodi(nitrile carbonate); 1,6,9-decanetri(nitrile carbonate); 1,3,6-heptanetri(nitrile carbonate); cyclohexyldi(nitrile carbonate); 4-bromo-1,6-hexanedi(nitrile carbonate); 2-chloro-1,9nonanedi(nitrile carbonate); dilinoleodi(nitrile carbonate); trilinoleotri(nitrile carbonate); etc. (Alternatively, the foregoing poly(nitrile carbonates) may be named as nitrile polycarbonates; for instance, fumarodi(nitrile carbonate) might also be designated as "fumaronitrile dicarbonate.")

The temperture for effecting the reaction of the polyhydroxamic acid and phosgene, or of the polyhydroxamic acid and thionyl chloride, may vary depending upon the particular polyhydroxamic acid selected, but in all cases should be conducted below the decomposition temperature of the desired cyclic compound. Reflux temperatures can also be used as long as the reflux temperature of the particular mixture is below the decomposition temperature of the corresponding poly(nitrile carbonate) or aliphatic poly(nitrile sulfite) produced. The reaction temperature will usually fall in the range of up to about 90°C., often up to about 40° to 70°C., preferably up to about 30°C. The reaction can be run at temperatures as low as about minus 30°C. Ordinarily the reaction will proceed readily at atmospheric pressure byt sub- and superatmospheric pressures can be employed if desired.

Either the polyhydroxamic acid reactant or the thionyl chloride (or phosgene, whichever is the case) can be in excess but it is preferred that at least a stoichiometric amount of thionyl chloride (or phosgene) be used, that is, a ratio of at least one mole of thionyl chloride (or phosgene) per hydroxamic acid substituent. A large excess of thionyl chloride (or phosgene) is particularly preferred. The reaction can be conducted in the liquid phase and in many cases, the polyhydroxamic acid will react from the solid state. Advantageously, the polyhydroxamic acid is first dissolved or slurried in an oxygen-containing organic solvent. Illustrative of suitable oxygen-containing solvents are the thionyl chloride (or phosgene) reactant itself and normally liquid organic ethers, esters, furans, dioxanes and the like. A preferred solvent is the thionyl chloride reactant, an excess of which will partially dissolve the polyhydroxamic acid.

The reaction is often over in less than about 0.5 hour, for example 15 minutes, or in about 5 to 20 hours, depending upon the reaction temperature employed, and is marked by a cessation in hydrogen chloride gas evolution. Normally at least about 0.5 hour is required for the reaction to go to completion at temperatures which minimize side reactions. The reaction is usually quite rapid as the polyhydroxamic acid is dissolved. At the lower reaction temperatures, the polyhydroxamic acid is generally slow to dissolve and may even come out of solution, go back into solution, etc., during the reaction.

The aliphatic or cycloaliphatic poly(nitrile sulfite) or poly(nitrile carbonate) can be recovered from the resulting solution by any desirable means, for instance, by first filtering the resulting solution to remove any unreacted starting materials and then subjecting the filtrate to reduced pressure to remove unreacted thionyl chloride (or phosgene) and inert solvent, if employed, and provide the cyclic compound as a crude product. Alternatively, prior to the filtering step, the solution can be cooled to crystallize out the product which is then recovered as described. The crude product, which can be either crystalline or liquid, depending on the particular poly(nitrile sulfite) or aliphatic poly(nitrile carbonate) prepared, contains small amounts of impurities relatively high in chlorine content. A purer product, essentially chlorine-free, can be obtained by recrystallization techniques as, for instance, from a suitable solvent such as dichloromethane, carbon disulfide, ethyl acetate, thionyl chloride (or phosgene) and the like, or mixtures thereof.

A convenient alternative method for obtaining an essentially chlorine-free aliphatic and cycloaliphatic poly(nitrile sulfite) or poly(nitrile carbonate) is by extraction or washing with a hydrocarbon solvent. Any normally liquid hydrocarbon solvent can be used for the extraction, as, for instance, alkanes of 5 to 15 or more carbon atoms, aromatic solvents such as benzene, xylenes, toluene, chlorobenzene and the like. A minimum amount of solvent is employed in the extraction, the actual amount used being dependent upon the particular poly(nitrile sulfite) or poly(nitrile carbonate) being treated. If desired, a combination of both the recrystallization and extraction methods can be used to obtain essentially chlorine-free yields of the cyclic compounds of the invention. Thermal decomposition of the essentially chlorine-free cyclic products results in improved yields of purer isocyanate products, which are also essentially chlorine-free.

The following examples are included to further illustrate the present invention.

EXAMPLE I

Fumarodi(nitrile sulfite)

To a 300 cc. fluted, round bottom flask, equipped with a reflux condenser attached to a $CaCl_2$ drying tube, were added 4.2 g. (0.029 mole) of fumarodihydroxamic acid and 248 g. (2.08 moles) of thionyl chloride. The reaction mixture was stirred mechanically and heated to reflux for half an hour. The resulting solution was filtered and the thionyl chloride removed under reduced pressure. There resulted a quantitative yield of crude fumarodi(nitrile sulfite), m.p. 149°–150°C. (decomposed). Recrystallization from benzene gave chlorine-free white needles, m.p.: 150°C. (dec.).

To a 500 cc. round bottom flask, equipped with a reflux condenser attached to a $CaCl_2$ drying tube, were added 12 g. (0.050 mole) of fumarodi(nitrile sulfite), prepared as above, and 200 cc. of o-dichlorobenzene. The reaction mixture was stirred mechanically and heated to reflux for 2 hours. The resulting solution was fractionally distilled to give 4.5 g. (82%) of chlorine-free trans-vinylenediisocyanate, b.p.: 152°–155°C. at 745 mm. of Hg pressure.

EXAMPLE II

Adipodi(nitrile sulfite)

To a 500 cc. fluted, round bottom flask, equipped with a reflux condenser attached to a $CaCl_2$ drying tube, were added 23.8 g. (0.14 mole) of adipodihydroxamic acid and 495 g. (4.16 moles) of thionyl chloride. The reaction mixture was stirred mechanically and heated to a maximum temperature of 55°C. for 2 hours. The resulting solution was filtered and the thionyl chloride removed under reduced pressure. There resulted a quantitative yield of crude adipodi(nitrile sulfite) which upon recrystallization from pentane gave chlorine-free white crystals, m.p.: 45°C.

The infrared spectrum ("Nujol" mull) of the recrystallized material showed a significant band at 6.19 microns, chracteristic of a C=N stretching vibration, and significant absorption in the 8.13 micron region, characteristic of cyclic sulfites.

Decomposition of the white crystals of adipodi(nitrile sulfite) in accordance with the procedure and apparatus of Example I provides chlorine-free butamethylenediisocyanate.

EXAMPLE III

Sebacodi(nitrile sulfite)

To a 500 cc. fluted, round bottom flask, equipped with a reflux condenser attached to a $CaCl_2$ drying tube, were added 28.0 g. (0.121 mole) of sebacodihydroxamic acid and 495 g. (4.16 moles) of thionyl chloride. The reaction mixture was stirred mechanically and maintained at a maximum temperature of 25°C. for 2 hours. The reaction mixture was filtered to give 5.9 g. of starting material. The thionyl chloride was removed under reduced pressure from the filtrate to give a quantitative yield of crude sulfite based on reacted starting material. The crude sebacodi(nitrile sulfite), m.p.: 47°–49°C., was recrystallized from pentane to give chlorine-free white crystals, m.p.: 48°–50°C.

Analysis Calc. for $C_{10}H_{16}N_2O_6S_2$: C, 37.05; H, 4.94; N, 8.65; S, 19.75. Found: C, 37.89; H, 5.50; N, 7.29.

The infrared spectrum (Nujol mull) of the recrystallized material showed a significant band at 6.19 microns, characteristic of a C=N stretching vibration, and significant absorption in the 8.15 micron region, characteristic of cyclic sulfites.

The sebacodi(nitrile sulfite) is decomposed to octamethylene diisocyanate employing the same procedure and apparatus of Example I.

EXAMPLE IV

Adipodi(nitrile carbonate)

To a 1 liter, fluted, round bottom flask, equipped with a reflux condenser attached to a CaCl₂ drying tube, were added 13.2 g. (0.075 mole) of adipodihydroxamic acid and 300 cc. of tetrahydrofuran. The mixture was stirred mechanically and heated to a maximum temperature of 41°C. for about 3 hours, during which time 121 g. (1.20 moles) of phosgene was introduced. The resulting solution was filtered and the solvents removed under reduced pressure. There was obtained a quantitative yield of crude adipodi(nitrile carbonate), m.p.: 61°–62°C. Recrystallization from a mixture of ether and pentane gave white chlorine-free needles, m.p.: 62°–63°C.

Analysis: Calc. for $C_8H_8N_2O_6$: C, 42.12; H, 3.53; N, 12.28; O, 42.07. Found: C, 42.33; H, 3.55.

The infrared spectrum (Nujol mull) of the recrystalized material was determined and showed a significant absorption peak at 6.12 microns, characteristic of conjugated C=N stretching vibrations, and a significant band in the 5.48 micron region, characteristic of cyclic carbonates.

Adipodi(nitrile carbonate) in the amount of 40.9 grams (0.179 mole) was dispersed in 247 grams of a liquid polyphenyl ether ("Monsanto OS-124") having a boiling point above 500°C. and the resulting mixture maintained at 70°C. The mixture was added dropwise over a period of about 1 to 1.5 hours to a flask kept under vacuum and containing 124 grams of the polyphenyl ether held at about 300°C. The temperature of the reaction was held at 260°–310°C. during the addition. The vacuum was held between about 0.02 to 5 mm. of Hg pressure during the addition and depended strongly upon the rate of addition of the carbonate solution. During the addition period, 21.9 grams (representing an 87% yield) of tetramethylenediisocyanate was collected overhead. The polyphenyl ether remained in the flask.

EXAMPLE V

Sebacodi(nitrile carbonate)

To a 500 cc., fluted, round bottom flask, equipped with a reflux condenser attached to a CaCl₂ drying tube, was added 5.7 g. (0.025 mole) of sebacodihydroxamic acid and 175 cc. of benzene. The mixture was stirred mechanically and heated to a maximum temperature of 55°–75°C., during which time 28 g. (0.28 mole) of phosgene was introduced. The resulting solution was filtered and the solvents removed under reduced pressure. There was obtained a quantitative yield of crude sebacodi(nitrile carbonate), m.p.: 42°–45°C. Recrystallization from a mixture of ether and pentane gave chlorine-free white needles, m.p.: 44°–45°C.

The infrared spectrum (Nujol mull) of the recrystalized sample was determined and showed a characteristic conjugated C=N band at 6.13 microns, and a significant peak at 5.48 microns, characteristic of cyclic carbonates.

EXAMPLE VI

Fumarodi(nitrile carbonate)

To a 3-liter, fluted, round bottom flask equipped with a dry ice reflux condenser were added 182.6 g. (1.25 moles) of furmarodihydroxamic acid and 500 cc. of tetrahydrofuran. A two-fold excess of phosgene was fed into the reaction mixture over a period of about two hours and the temperature of the reaction was maintained at about room temperature. The reaction mixture was allowed to stand overnight, whereupon the product was separated from unreacted starting material. There resulted a 66.9% yield of chlorine-free recrystllized (from toluene) fumarodi(nitrile cabonate), m.p.: 163°–165°C. Yield of product is based on reacted starting material.

The infrared spectrum (Nujol mull) of the product showed the typical nitrile carbonate absorptions. The product gave the following data upon analysis:

Calculated: C, 36.38%; H, 1.02%; N, 14.14%. Found: C, 36.70%; H, 1.42%; N, 12.63%.

EXAMPLE VII

Japanodi(nitrile sulfite)

To a 500 cc. fluted, round bottom flask, equipped with a reflux condenser attached to a CaCl₂ drying tube, is added 35.8 g. (0.10 mole) of japanodihydroxamic acid, $HOHNOC(CH_2)_{17}CONHOH$, and 248 g. (2.08 moles) of thionyl chloride. The reaction mixture is stirred mechanically and heated to about 55°C. for 2 hours. The resultant solution is filtered and the thionyl chloride removed under reduced pressure. There results a quantitative yield of crude japanodi(nitrile sulfite).

EXAMPLE VIII

Trilinoleotri(nitrile sulfite)

To a 500 cc. fluted, round bottom flask, equipped with a reflux condenser attached to a CaCl₂ drying tube, is added 85 g. (0.10 mole) of trilinoleotrihydroxamic acid and 248 g. (2.02 moles) of thionyl chloride. The reaction mixture is stirred mechanically and heated to about 55°C. for 2 hours. The resultant solution is filtered and the thionyl chloride removed under reduced pressure. There results a quantitative yield of crude trilinoleotri(nitrile sulfite).

We claim:

1. A compound selected from the group consisting of: malonodi(nitrile carbonate); malonodi(nitrile sulfite); succinodi(nitrile carbonate); succinodi(nitrile sulfite); glutarodi(nitrile carbonate); glutarodi(nitrile sulfite); adipodi(nitrile carbonate); adipodi(nitrile sulfite); pimelodi(nitrile carbonate); pimelodi(nitrile sulfite); suberodi(nitrile carbonate); suberodi(nitrile sulfite); azelaodi(nitrile carbonate); cetylmalonodi(nitrile carbonate); cetylmalonodi(nitrile sulfite); thapsodi(nitrile carbonate); thapsodi(nitrile sulfite); japanodi(nitrile carbonate); japanodi(nitrile sulfite); cyclohexyldi(nitrile carbonate); cyclohexyldi(nitrile sulfite); 4-bromo-1,6-hexanedi(nitrile carbonate); 4-bromo-1,6-hexanedi(nitrile sulfite); 2-chloro-1,9-nonanedi(nitrile carbonate); 2-chloro-1,9-nonanedi(nitrile sulfite).

2. Adipodi(nitrile sulfite).
3. Japanodi(nitrile sulfite).
4. Adipodi(nitrile carbonate).
5. Compositions of matter having the structural formula:

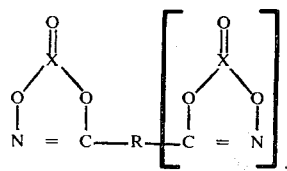

wherein R is an unsubstituted straight chain aliphatic hydrocarbon of 1 to 30 carbon atoms, X is sulfur or carbon, and no two cyclic nitrile functional groups are attached to the same carbon atom.

6. A compound selected from the group consisting of: 1,6,9-decanetri(nitrile carbonate); 1,6,9-decanetri(nitrile sulfite); 1,3,6-heptanetri(nitrile carbonate); 1,3,6-heptanetri(nitrile sulfite); trilinoleotri(nitrile carbonate); trilinoleotri(nitrile sulfite).

* * * * *